United States Patent
Kilian et al.

(10) Patent No.: US 6,921,485 B2
(45) Date of Patent: Jul. 26, 2005

(54) TWO PHASE ANAEROBIC ORGANIC MATTER TREATMENT AND SYSTEM

(76) Inventors: Rodolfo Ernesto Kilian, 21 Picket La., Aliso Viejo, CA (US) 92656; Allen Craig Todd, 16412 Ardsley Cir., Huntington Beach, CA (US) 92649

( * ) Notice: Subject to any disclaimer, the term of this patent is extended or adjusted under 35 U.S.C. 154(b) by 15 days.

(21) Appl. No.: 10/392,434

(22) Filed: Mar. 19, 2003

(65) Prior Publication Data

US 2004/0182779 A1 Sep. 23, 2004

(51) Int. Cl.$^7$ .............................. C02F 3/28; C02F 11/04
(52) U.S. Cl. .................... 210/603; 210/609; 210/195.3; 210/259
(58) Field of Search ................................ 210/603, 609, 210/629, 195.2, 195.3, 197, 252, 259, 908; 435/262, 262.5

(56) References Cited

U.S. PATENT DOCUMENTS

| | | | | |
|---|---|---|---|---|
| 4,067,801 A | * | 1/1978 | Ishida et al. ................. 210/603 |
| 4,597,872 A | * | 7/1986 | Andersson et al. ........ 210/605 |
| 4,652,374 A | * | 3/1987 | Cohen ......................... 210/603 |
| 4,659,471 A | * | 4/1987 | Molin et al. ................. 210/603 |
| 4,722,741 A | * | 2/1988 | Hayes et al. ............... 48/197 A |
| 4,735,724 A | | 4/1988 | Chynoweth .................. 210/603 |
| 4,936,996 A | * | 6/1990 | Messing ....................... 210/603 |
| 4,968,427 A | * | 11/1990 | Glanser et al. ............. 210/610 |
| 5,500,123 A | | 3/1996 | Sprivastava .................. 210/603 |
| 5,591,342 A | * | 1/1997 | Delporte et al. ............ 210/603 |
| 5,670,047 A | * | 9/1997 | Burke ........................... 210/603 |
| 6,036,862 A | | 3/2000 | Stover ......................... 210/603 |
| 6,113,786 A | | 9/2000 | Burke ........................... 210/603 |
| 6,254,775 B1 | | 7/2001 | McElvaney .................. 210/603 |
| 6,309,547 B1 | | 10/2001 | Burke ........................... 210/603 |
| 6,342,378 B1 | | 1/2002 | Zhang .......................... 435/168 |
| 6,416,993 B1 | | 7/2002 | Wexler ....................... 435/262.5 |
| 6,454,944 B1 | | 9/2002 | Raven ......................... 210/603 |
| 6,464,875 B1 | | 10/2002 | Woodruff ..................... 210/603 |
| 6,465,240 B1 | | 10/2002 | Wexler ....................... 435/262.5 |

FOREIGN PATENT DOCUMENTS

| | | | |
|---|---|---|---|
| JP | 62-279893 | * | 12/1987 |
| JP | 2-207899 | * | 8/1990 |

* cited by examiner

Primary Examiner—Fred G. Prince
(74) Attorney, Agent, or Firm—Dennis W. Beech

(57) ABSTRACT

The process and system may have an organic matter influent introduced into an acid reactor. The acid reactor may be maintained under conditions to facilitate creation of volatile acids in a fluid having water and suspended solids forming a sludge effluent. The sludge effluent may be communicated to an acid separation element where the water and volatile acids may be separated from the suspended solids. A liquid stream may be communicated from the acid separation element to a methane reactor and a solids recycle stream may be communicated to the acid reactor. The methane reactor may be maintained under conditions to facilitate creation of biogas. A liquid effluent may be communicated from the methane reactor to a methane separation element where liquid water may be separated from the solids. A second solids recycle may be communicated from the methane separation element to the methane reactor.

2 Claims, 1 Drawing Sheet

TWO PHASE ANAEROBIC ORGANIC MATTER TREATMENT AND SYSTEM

BACKGROUND OF THE INVENTION

This invention relates to systems and processes for treatment of organic matter that may be waste such as sewage, sludge in municipal refuse and the like, biomass material such as plants and crop waste or other organic source matter that may be converted to biogas and other products. The new system and process is a two phase process that may control the acid forming organisms in an acid reactor and the methane forming mechanisms in a methane reactor to control the hydraulic retention time requirements of the process.

Anaerobic two phase digestion processes have been known in the industry for processing organic matter to produce methane gas and other products. The anaerobic digestion may be carried out in a single reactor or in a two stage reactor wherein both involve the two phase, acid forming and methane forming, method of processing the organic matter. The organic matter may be waste or non-waste matter, but may normally be waste products. The waste products may be sewage, municipal refuse, food waste, biomass such as plants, crops, plant and crop wastes and the like, and industrial liquid and solids waste.

These anaerobic two phase digestion processes may have been limited in their use due to the long retention times required for the anaerobic organisms to grow and process the organic matter. For complete mix reactors, the process may be slow and expensive due to the need for large reactors to process economical amounts of organic matter given the time required for microorganisms to grow and digest the organic matter into methane, carbon dioxide and other products. The large reactors may be required because of the large quantity of liquid as compared to solid material that must be retained in a reactor, the hydraulic retention time.

The separation of the anaerobic process into the acidogenesis phase, the hydrolization of volatile suspended solids and the conversion of these into volatile fatty acids, and the methanogenesis phase, the conversion of the volatile fatty acids into methane and carbon dioxide, may have improved operation and performance of the process. However, the hydraulic retention time and the solid retention time associated with each reactor process may still be approximately equal thereby requiring large reactors because of overall fluid retention time.

There may have been some improvement in the anaerobic two phase digestion process to preprocess the organic matter influent introduced into the process and in the feedback of the methane phase reactor effluent to be reintroduced into the methane phase reactor. While such treatment may include stripping of carbon dioxide and hydrogen sulfide from the effluent as well as the introduction of small amounts of oxygen, the return of the effluent to the methane phase reactor may only improve methane gas production, but not significantly reduce retention times.

If hydraulic retention times can be reduced, wherein the large volume reactors may not be necessary for such fluid retention, then the cost associated with the use of large reactors to produce proportional quantities of product gasses and other effluent may be reduced to allow for an improved, economical, more efficient anaerobic two phase digestion process.

SUMMARY OF THE INVENTION

The present invention is directed to systems and methods for treating organic matter influent in an anaerobic two phase digestion system. An organic matter influent may be introduced into an acid reactor. The acid reactor may be maintained under conditions to facilitate creation of volatile acids in a fluid having water and suspended solids forming a sludge effluent. The sludge effluent may be communicated to an acid separation element where the water and volatile acids may be separated from the suspended solids. A liquid stream may be communicated from the acid separation element to a methane reactor and a solids recycle stream may be communicated to the acid reactor.

The methane reactor may be maintained under conditions to facilitate creation of biogas. A liquid effluent may be communicated from the methane reactor to a methane separation element where liquid, principally water, may be separated from the solids. A second solids recycle may be communicated from the methane separation element to the methane reactor and a biogas may be communicated from the methane reactor. Excess solids may be discharged from the system.

These and other features, aspects and advantages of the present invention will become better understood with reference to the following drawings, description and claims.

DETAILED DESCRIPTION

Figure 1:
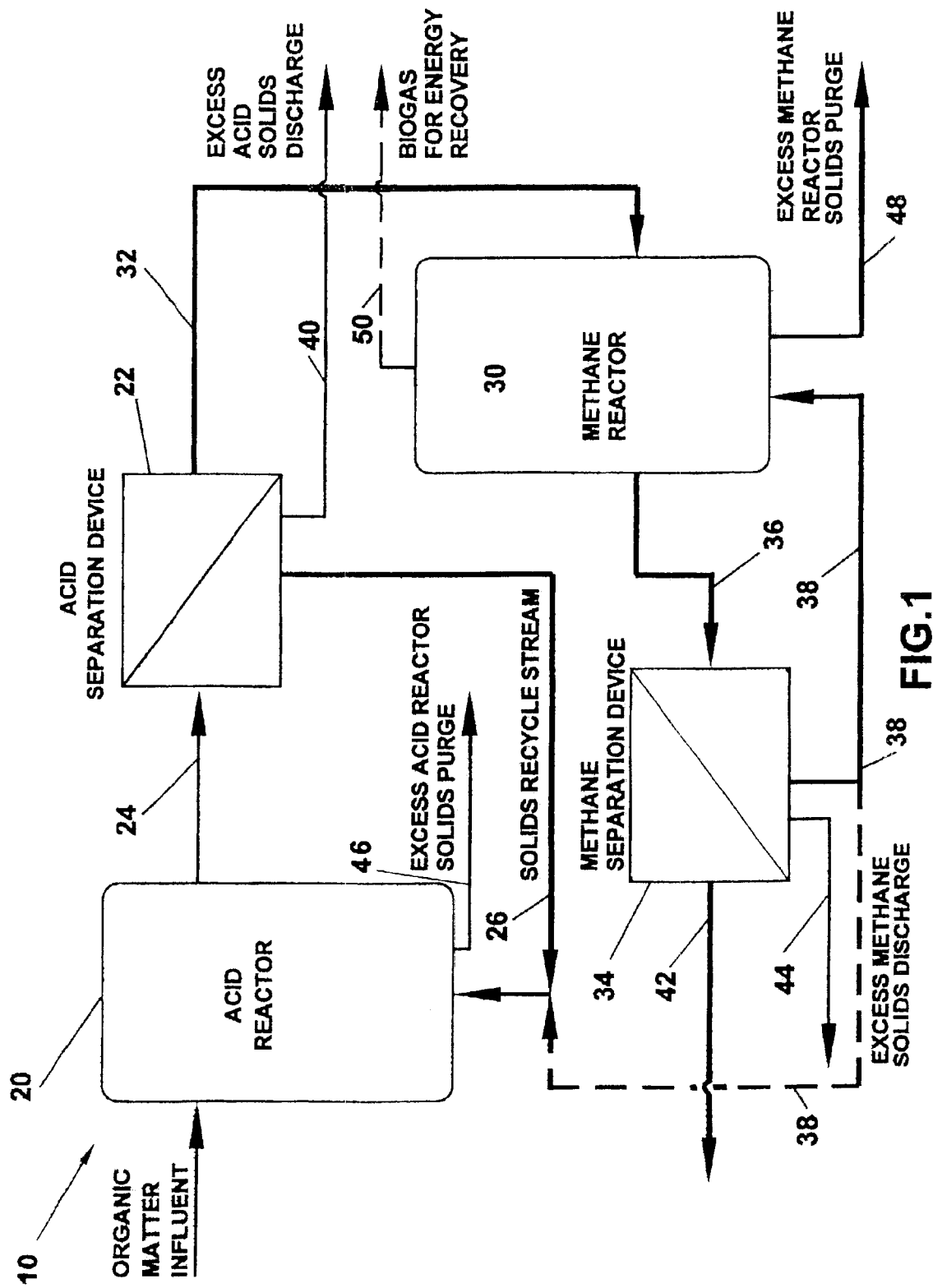
FIG. 1 illustrates a functional diagram of an anaerobic two phase digestion process with separation elements to control hydraulic retention time according to an embodiment of the invention.

The following detailed description represents the best currently contemplated modes for carrying out the invention. The description is not to be taken in a limiting sense, but is made merely for the purpose of illustrating the general principles of the invention.

Referring to FIG. 1, an anaerobic organic matter digestion process 10 may be a two phase process having an acid reactor 20 phase and a methane reactor 30 phase. The acid reactor 20 may be a mix tank or series of tanks that receives the organic matter influent. The hydraulic retention time of the acid reactor may be approximately 1 hour to 3 days depending on the velocity of conversion of the organic matter into volatile fatty acids as compared to a solids retention time of 1 day to 5 days. The conditions in the acid reactor 20 with volatile acids content of approximately 3,500 to 20,000 mg/l may be a pH of approximately 5.0 to 7.0 and a temperature of approximately 80 degrees to 155 degrees Fahrenheit.

The acid reactor 20 may be in fluid communication with an acid separation element 22 with the sludge effluent 24 communicated to the acid separation element 22. The acid separation element 22 may have a solids barrier, a physical or mechanical barrier such as a membrane, that may permit passage of the fluid having water and volatile acids and inhibit passage of solid matter. Separation of solids may also be accomplished by centrifugation or other technology that does not have a physical or mechanical barrier. The acid phase bacterial matter and the undegraded solids may be recycled to the acid reactor 20 to maintain the microbial population for use in degrading the volatile solids.

The thickened sludge or solids recycle stream 26 may be communicated from the acid separation element 22 to the acid reactor 20. Excess solids, for example, undegradable organics and nonvolatile solids may be wasted as excess acid solids discharge 40. Also, excess acid reactor solids purge 46 may be wasted from the system. Excess solids may be discharged based on the concentration of inorganic or inert solids that are present and based on the capability of the separation elements to separate the solids from the liquid.

The acid separation element 22 may be in fluid communication with a methane reactor 30. The liquid stream 32, primarily water and volatile acids, may be conveyed to the methane reactor 30 where bacteria may convert the volatile fatty acids into methane and carbon dioxide. The methane reactor 30 may be a tank or series of tanks or vessels. The methane reactor 30 operating conditions may be a pH of approximately 7.0 to 9.0 and a temperature of approximately 80 degrees to 155 degrees Fahrenheit. Total volatile acid content may be approximately 0 to 1,500 mg/l. The hydraulic retention time may be 2 hours to 18 days as compared to a solids retention time of 10 days to 40 days. Methane gas and carbon dioxide or biogas 50 created may be discharged for energy recovery.

The methane reactor 30 may be in fluid communication with a methane separation element 34 with the liquid effluent 36 communicated to the methane separation element 34. The methane separation element 34 may have a solids barrier, a physical or mechanical barrier such as a membrane, that may permit passage of the liquid, principally water, and inhibit passage of the solids. Separation of solids may also be accomplished by centrifugation or other technology that does not have a physical or mechanical barrier. The methane phase bacterial matter and undegraded solids may be recycled as a solids recycle stream 38 to the methane reactor 30 with an option of being recycled to the acid reactor 20 for further degradation. Excess solids, such as microorganisms and inorganic solids generated, may be wasted from the methane separation element 34 as excess methane solids discharge 44 from the system. Excess solids may also be wasted directly from the methane reactor 30 as excess methane reactor solids purge 48. The water 42, may also be discharged.

While the invention has been particularly shown and described with respect to the illustrated embodiments thereof, it will be understood by those skilled in the art that the foregoing and other changes in form and details may be made therein without departing from the spirit and scope of the invention.

We claim:

1. A method for treating an organic matter influent, comprising the steps of:

provifing an organic matter influent to be treated by an anaerobic two phase digestion system to an acid reactor;

maintaining conditions in said acid reactor to facilitate creation of a volatile acid in a fluid having a water and a suspended solids content forming a sludge effluent;

communicating said sludge effluent to an acid separation element;

separating said water and said volatile acid from said suspended solids;

communication a liquid stream from said acid separation element to a methane reactor;

communication a solids recycle stream from said acid separation element to said acid reactor;

maintaining conditions in said methane reactor to facilitate creation of a biogas;

communicating a liquid effluent from said methane reactor to a methane separation element;

separating a liquid from a solids;

communicating a portion of a second solids recycle stream from said methane separation element to said methane reactor and communicating a portion of said second solids recycle stream from said methane separation element to said acid reactor;

communicating said biogas from said methane reactor; and discharging a first excess solids discharge from said acid reactor and from said acid separation element, and a second excess solids discharge from said methane reactor and from said methane separation element.

2. A system for treating an organic matter influent comprising:

an acid reactor in communication with an acid separation element;

said acid separation unit in communication with a methane reactor and having a recycle communication link with said acid reactor;

said methane reactor producing a biogas discharge and in communication with a methane separation element;

said methane separation element having a first recycle communication link with said methane reactor and a second recycle communication link with said acid reactor; and a first discharge for a first excess solids discharge from said acid reactor and from said acid separation unit, and a second discharge for a second excess solids discharge from said methane reactor and from said methane separation element.

* * * * *